United States Patent
Froix

(10) Patent No.: US 6,248,129 B1
(45) Date of Patent: *Jun. 19, 2001

(54) EXPANDABLE POLYMERIC STENT WITH MEMORY AND DELIVERY APPARATUS AND METHOD

(75) Inventor: Michael Froix, Mountain View, CA (US)

(73) Assignee: Quanam Medical Corporation, Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/177,917

(22) Filed: Oct. 23, 1998

Related U.S. Application Data

(63) Continuation-in-part of application No. 08/749,562, filed on Nov. 15, 1996, now abandoned, which is a continuation-in-part of application No. 08/516,091, filed on Aug. 17, 1995, now Pat. No. 5,607,467, which is a continuation of application No. 07/874,181, filed on Apr. 24, 1992, now Pat. No. 5,258,020, which is a continuation of application No. 07/582,521, filed on Sep. 14, 1990, now Pat. No. 5,163,952.

(51) Int. Cl.⁷ ......................................... A61F 2/06
(52) U.S. Cl. ................................................ 623/1.42
(58) Field of Search ................. 623/1, 12, 1.39, 623/1.42, 1.4, 1.45, 1.49

(56) References Cited

U.S. PATENT DOCUMENTS

| 4,871,758 | | 10/1989 | Froix | 523/106 |
|---|---|---|---|---|
| 4,904,272 | * | 2/1990 | Middleton et al. | 623/1 |
| 4,921,495 | * | 5/1990 | Kira | 623/1 |
| 4,979,959 | | 12/1990 | Guire | 623/66 |
| 5,019,096 | | 5/1991 | Fox, Jr. et al. | 623/1 |
| 5,059,211 | * | 10/1991 | Stack et al. | 623/1 |
| 5,163,952 | * | 11/1992 | Froix | 623/1 |
| 5,258,020 | * | 11/1993 | Froix | 623/1 |
| 5,607,467 | * | 3/1997 | Froix | 623/1 |
| 5,665,114 | * | 9/1997 | Weadock et al. | 623/1 |
| 5,957,971 | * | 9/1999 | Schwartz | 623/1 |
| 5,962,007 | * | 10/1999 | Cooper et al. | 623/1 |
| 5,972,027 | * | 10/1999 | Johnson | 623/1.4 |

FOREIGN PATENT DOCUMENTS

| 2035350A | 6/1980 | (GB) . |
|---|---|---|
| 2139898A | 11/1984 | (GB) . |

OTHER PUBLICATIONS

Stein, C.A. et al., "Oligodeoxynucleotides as Inhibitors of Gene Expression: A Review", Cancer Research 43, 2659–2668, May 15, 1988.

* cited by examiner

*Primary Examiner*—David H. Willse
*Assistant Examiner*—Suzette J. Jackson
(74) *Attorney, Agent, or Firm*—Flehr Hohbach Test Albritton & Herbert LLP

(57) ABSTRACT

A stent for use in a lumen defined by a wall of a vessel of a patient having a body. The vessel is comprised of a hollow substantially cylindrical member formed of a biocompatible composition. The composition incorporates at least one medical agent in a weight up to 90% of the total weight of the stent so that at least one medical agent is released from the composition of the stent into the vessel at a controlled rate extending over a period of time after the stent is inserted into the vessel.

28 Claims, 4 Drawing Sheets

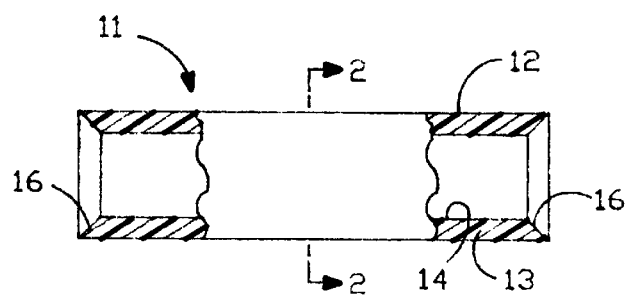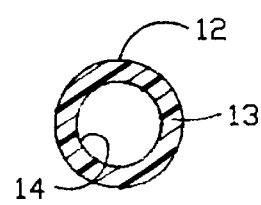
FIG.-1  FIG.-2
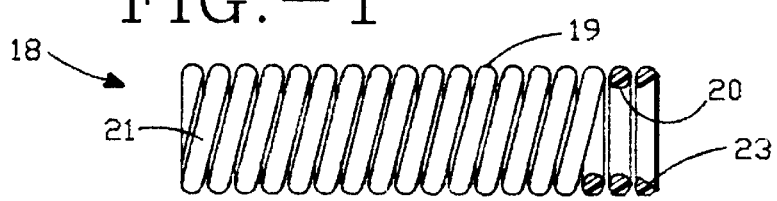
FIG.-3
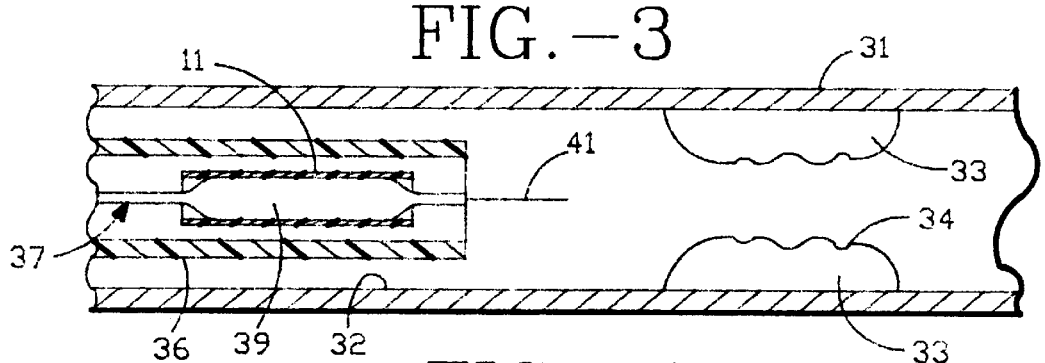
FIG.-4
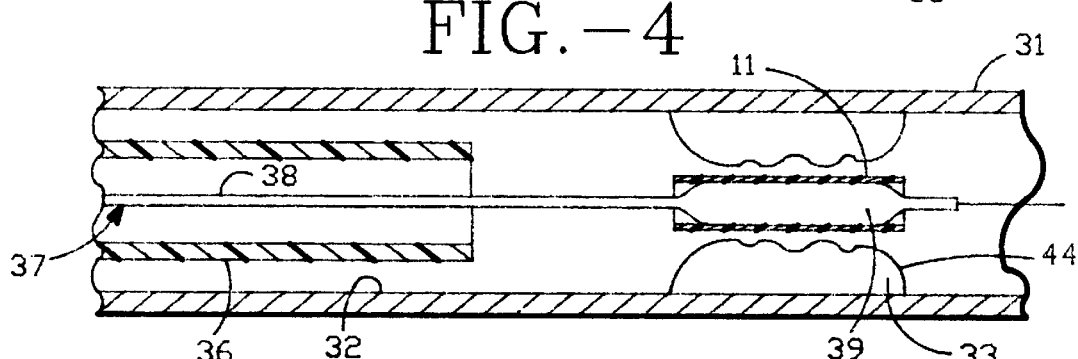
FIG.-5
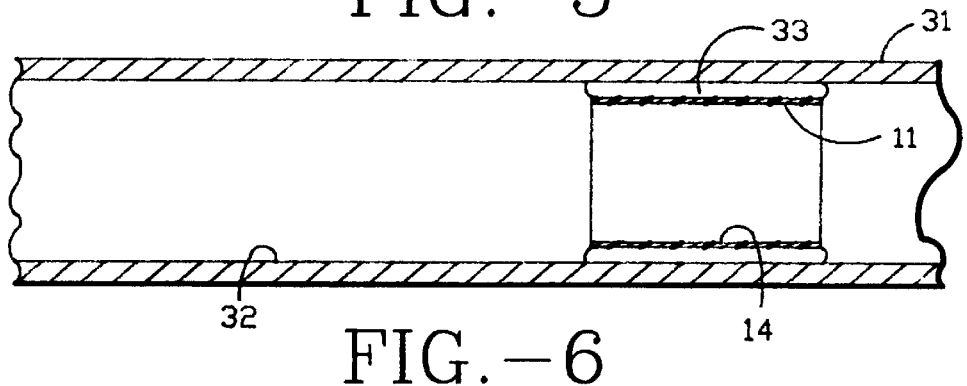
FIG.-6

EXPANDABLE POLYMERIC STENT WITH MEMORY AND DELIVERY APPARATUS AND METHOD

This is a continuation-in-part of application Ser. No. 08/749,562, filed Nov. 15, 1996 now abandoned, which is a continuation-in-part of application Ser. No. 08/516,091 filed Aug. 17, 1995 now U.S. Pat. No. 5,607,467, which is a continuation of application Ser. No. 07/874,181 filed Apr. 24, 1992, now U.S. Pat. No. 5,258,020, which is a continuation of application Ser. No. 07/582,521 filed Sep. 14, 1990, now U.S. Pat. No. 5,163,952.

This invention relates to an expandable polymeric stent with built-in elastic memory and delivery apparatus and method for use therewith.

Many different types of stents have heretofore been provided. For example, stents have been provided to attempt to prevent post-angioplasty vessel reclosure. Typically, such intravascular stents have been utilized in the region of the stenosis to maintain the passageway through the stenosis. Such stents usually have been formed of metal. Such metal stents have been found to be intrinsically thrombogenic because of their net surface charge and surface irregularities. In addition, expandable metal stents have created vessel wall thinning as well as intimal hyperplasia within the stent and at the borders of the stent. These can be caused by uneven circumferential contact of the stent with the vessel endoluminal surface, compliance mismatch between the stent and the vessel wall and excessive stent stiffness. A stent formed of plastic is disclosed in U.S. Pat. No. 4,820,298. As disclosed therein, a thermoplastic polyester polycarbonate copolymer is formed into a helical coil by providing a linear extrusion and winding the same on a mandril and reheating to form a helical spring coil. Strand material is secured to the helical coil. The stent is inserted with a stylet. When the stylet is removed, the stent expands under its recovery memory to assume a helical configuration. This recovery memory is based upon the fact that it was formed from a linear strip and wound onto a mandril which resulted in stored energy, causing it to expand into a helix when released from the stylet. The adjacent loops of the helical stent are constrained by the strand material which has been secured thereto. It is believed that even though such a stent is formed of plastic, it has a number of disadvantages making it unsuitable for use in many applications. It is necessary to mechanically restrain the stent to prevent it from expanding prior to insertion into the vessel. Also it is believed that it is hard to predict the expansion forces exerted when it is released.

In addition to mechanical stenting, pharmacological treatment is necessary to prevent restenosis. Conventional systemic drug delivery, however, is often ineffective in comparison to drug delivery that is localized to the specific site where therapy is needed. Systemic administration too often results in a drug's elimination in the blood or liver before it reaches its target site. Localized delivery, directly to the cells that need the drug, is more potent and reliable. U.S. Pat. No. 5,019,096 discloses the use of antimicrobial containing polymer solutions on surfaces of infection-resistant medical devices to effect a slow, localized release of said antimicrobial agents. Similarly, U.S. Pat. No. 4,979,959 discloses attaching growth hormones or an antithrombogenic agent to the surface of synthetic blood vessels in order to make them more biocompatible. Surface adsorption of drugs, however, can only provide small amounts for delivery. In addition, the literature describes controlled drug release implants for localized drug delivery wherein said implants are prepared by dispersing drugs in polymeric matrices. There is, however, no teaching of a medical device which incorporates the dual functions of vascular stenting and localized drug delivery wherein a drug is contained in other than a surface coating of said device and wherein the drug is for a purpose other than that of enhancing biocompatability of the device. There is therefore a need for an improved stent that carries and delivers drugs locally while it simultaneously functions mechanically.

In general it is an object of the present invention to provide a plastic stent which carries and delivers drugs locally while it functions as a stent, a delivery apparatus and method for use with the same.

In general it is another object of the present invention to provide a plastic stent which has a built-in elastic memory, a delivery apparatus and method for use with the same.

Another object of the invention is to provide a stent of the above character which is self-restrained permitting it to be readily inserted into a vessel of a patient.

Another object of the invention is to provide a stent of the above character which has low protein adsorption and is biocompatible.

Another object of the invention is to provide a stent of the above character which need not be physically constrained from expansion prior to placement in the vessel of a patient.

Another object of the invention is to provide a stent of the above character which can be provided with a predetermined stiffness to match the compliance of the vessel.

Another object of the invention is to provide a stent of the above character which can be provided with a surface which facilitates intimal and endothelial cell growth to enhance the biocompatibility of the stent.

Another object of the invention is to provide a stent of the above character which can carry medical agents such as thrombolytic agents, growth factors, and slow release medications.

Another object of the invention is to provide a stent of the above character which will expand to a greater diameter upon being subjected to an external factor.

Another object of the invention is to provide a stent of the above character which has a thermal transition incorporated therein.

Another object of the invention is to provide a stent of the above character which has been crosslinked.

Another object of the invention is to provide a stent of the above character which can be readily and economically manufactured.

Another object of the invention is to provide a stent of the above character which can be readily positioned in the desired location in the vessel of the patient.

Additional objects and features of the invention will appear from the following description in which the preferred embodiments are set forth in conjunction with the accompanying drawings.

FIG. 1 is a side elevational view partially in cross section of a stent incorporating the present invention.

FIG. 2 is cross sectional view taken along the line 2—2 of FIG. 1.

FIG. 3 is a side elevational view partially in cross-section of another embodiment of a stent incorporating the present invention.

FIG. 4 is a cross sectional view of a vessel showing the delivery apparatus for delivering a stent of the type shown in FIG. 1 into a stenosis into the vessel.

FIG. 5 is a cross sectional view similar to FIG. 4, but showing the stent delivered into the stenosis in the vessel.

FIG. 6 is a cross sectional view similar to that shown in FIG. 5 showing the stent in an expanded condition within the stenosis and with the delivery apparatus removed from the vessel.

Figures 7, 8:
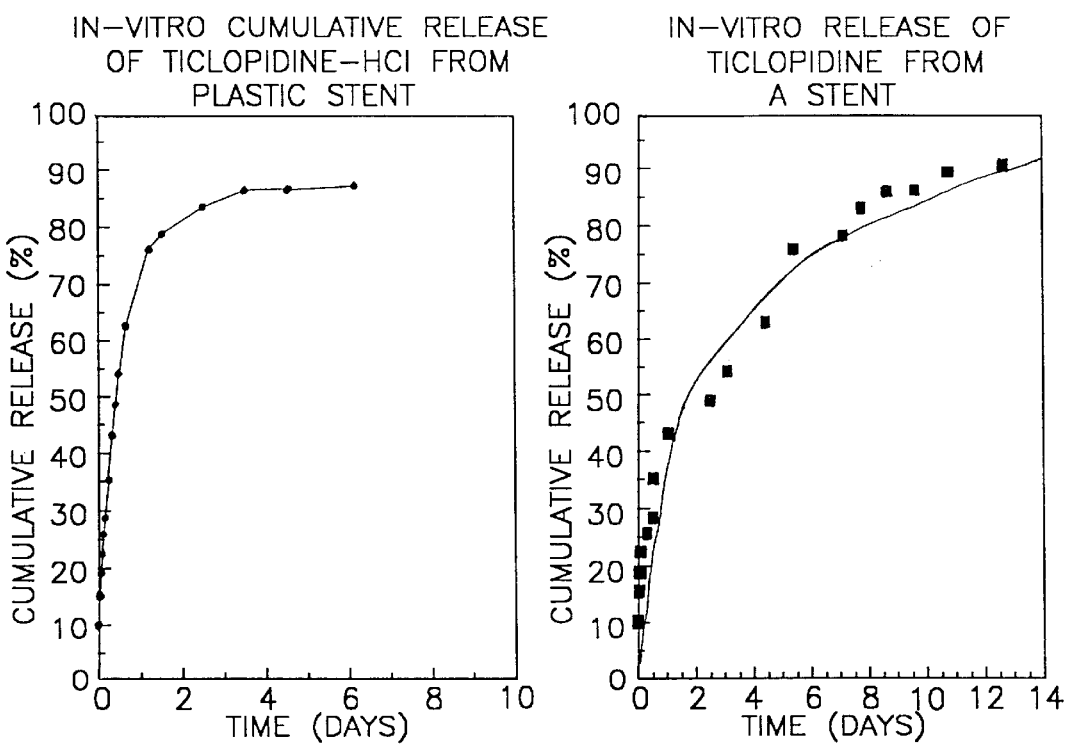
FIG. 7 is a graph demonstrating the in vitro cumulative release of dispersed Ticlopidine from polymer stent material as a function of time.
FIG. 8 is a graph demonstrating the in vitro cumulative release of dispersed, encapsulated Ticlopidine from polymer stent material as a function of time.

In general, the stent of the present invention is for use in the lumen of a vessel of a patient having a body with the vessel therein. The stent is comprised of substantially a cylindrical member formed of a plastic material. The stent has a predetermined diameter and has a memory provided therein of a diameter greater than the predetermined diameter. The plastic is characterized in that it will attempt to assume the greater diameter in its memory upon occurrence of one or more of the following conditions:

(a) adsorption of heat by the plastic;

(b) adsorption of liquid by the plastic; and (c) a change in pH in the liquid in contact with the plastic.

In the delivery apparatus and method, a balloon catheter is utilized for delivering the stent to the desired site. When the balloon with the stent thereon has been delivered to the desired site, the balloon can be inflated to help expand the stent when the stent is subjected to certain factors and conditions. Thereafter the balloon is deflated and the balloon catheter is removed leaving the stent in place. The stent is caused to assume the greater diameter of its memory by the adsorption of heat by the plastic, the adsorption of liquid by the plastic, or a change in the pH in the liquid surrounding the plastic.

As more particularly shown in the drawings, the stent 11 as shown in FIGS. 1 and 2 is in the form of a generally cylindrical tubular member 12 made of plastic. It is provided with a cylindrical wall 13 which forms a flow passage or lumen 14 extending therethrough. The ends of the member 12 are provided with chamfers 16 as shown.

It should be appreciated that although the cylindrical wall 13 has been shown to be continuous it can be discontinuous as desired. For example, it can be in the form of a helix as shown in FIG. 3 in which the stent 18 in the form of a cylindrical member 19 is formed by turns or loops 21 with a lumen 20 extending therethrough and with chamfers 23 provided at opposite ends. It should be appreciated that other constructions, if desired, can be utilized, as for example one having a perforated wall with openings or holes of various sizes therein.

The member 12 is formed of a plastic material and has a predetermined diameter. The material is of a type which has a built-in elastic memory of a diameter greater than the predetermined diameter. The size, diameter and length of the stent is tailored to the application for which the stent is to be utilized. For example, for cardiovascular applications the stent can have a length ranging from 0.5 cm to approximately 3 cm. It can have a diameter ranging from 0.50 mm to 20 mm with a wall thickness ranging from 0.01 to 0.5 mm. In order to facilitate its introduction into a vessel, the diameter of the stent is reduced by a suitable amount, as for example 10 to 30 percent. However, it should be appreciated that, if desired, the reduction can be sufficiently great so that when the stent returns to its original expanded state it could have expanded by 400 to 500 percent from its predetermined diameter.

In accordance with the present invention, in order to have the stent expand to a diameter greater than the predetermined diameter, the stent is provided with a built-in elastic memory. This built-in elastic memory is achieved by utilizing a plastic such as a polymer that has a molecular transition incorporated in the same. The polymeric material is biocompatible. The polymeric material is compounded in such a manner so that the achieved built-in memory can be activated upon subjecting the stent to certain factors as hereinafter explained, which may include adsorption of heat by the plastic, adsorption of liquid by the plastic and a change in the pH in the liquid in which the plastic is disposed. In order to make it responsive to the adsorption of a liquid, it is desirable that the polymeric material possess a range of hydrophilicities ranging from 0 to 50 percent and preferably from 0 to 30 percent. The molecular transitions which can be incorporated in the stent can be in the form of thermal transitions, as for example a crystal melting point between $-50°$ C. and $+100°$ C. of the polymer main chain, and a melting point of between $-50°$ C. and $+100°$ C. of a side chain of the polymer capable of crystallizing, a glass transition temperature between $-50°$ C. and $+100°$ C. and a liquid-crystal phase (mesophase) temperature transition between $-50°$ C. and $+100°$ C. The molecular transitions can also include a local mode molecular transition also accessed by heat.

In accordance with the present invention, various formulations can be utilized for preparing polymeric materials which can be utilized for achieving built-in elastic memories in stents of the present invention. The types of formulations which can be used are set forth in the examples below.

EXAMPLE 1

| Glass Transition Formulation Using a UV Initiator | |
|---|---|
| Methyl methacrylate | 4.5 grams |
| Polyethyleneglycol methacrylate | 3.2 grams |
| Butyl methacrylate | 2.0 grams |
| Hexanedioldimethacrylate | 0.3 gram |
| Benzoin methyl ether | 0.03 gram |

All monomers are mixed and then introduced into a transparent spinning tube in a sufficient quantity to provide a desired length of tube with a desired wall thickness. The benzoin methyl ether is a UV initiator. While spinning the tube, an ultraviolet light source is turned on to direct ultraviolet light onto the spinning tube to initiate polymerization. It can be appreciated that the wall thickness of the tube is determined by the amount of monomers placed in the tube as well as the rate of spin of the tube. After the tube has been cured it is removed. It is then raised to a temperature of approximately 37° C., which is slightly above the glass transition temperature for the mixture of Example 1. Assuming that the tube had a original diameter of 3 mm, the tube is stretched to reduce the final outside diameter of the tube to 1 mm. As soon as the desired predetermined diameter has been reached, the temperature of the stent is lowered to a suitable lower temperature, as for example 23° C., while holding the tube in the stretched condition to provide a tube which has a predetermined outside diameter. The appropriate length is cut from the tube and the ends are ground to provide the chamfers 16 on the ends as shown on FIG. 1. The stent is then ready to be positioned in a vessel of a patient in a manner hereinafter described. The stent is then raised to the transition temperature of 37° C. in a manner hereinafter described which causes the stent to attempt to assume the original or greater diameter in its memory, in other words to recover its original condition.

The tube hereinbefore described is manufactured in what can be considered to be a batch process. It is desired to manufacture the tube in a continuous manner. This can be accomplished by polymerizing the monomers into a polymer, pelleting the polymer and feeding the polymer, the crosslinking agent and the UV initiator through a conventional extruder to provide a continuous length of tubing which can be subjected to ultraviolet light to crosslink the extruded tube. The tube can be then be cut into suitable lengths to provide the stents in which the ends are ground and then the stent stretched at the temperature slightly above the glass transition temperature to decrease the diameter to an appropriate diameter, as for example the outside diameter of 1 mm hereinbefore described. The stent can thereafter be utilized in the same manner as the stent which is formed from the liquid monomers.

EXAMPLE 2

| Glass Transition Formulation Polymerized by a Thermal Initiator | |
| --- | --- |
| Isobornyl methacrylate | 3.5 grams |
| Hexafluorobutyl methacrylate | 2.6 grams |
| Dodecyl methacrylate | 3.5 grams |
| Butanediol dimethacrylate | 0.04 gram |
| 2,2,Azobis (2-methyl propionitrile) (AIBN) | 0.004 gram |

The first four monomers listed can be mixed and degassed with nitrogen, after which the last ingredient, a thermal initiator, is introduced into the mixture, the is mixture being introduced into the spinning tube as hereinbefore described and raising the spinning tube with the material therein to a suitable temperature such as for example 65° C. After polymerization, the tube is cut into suitable lengths to form stents which have their ends ground. The stents are then stretched at an elevated temperature as for example 40° C., and held in that stretched state until they have been cooled to approximately 20° C. By way of example, the pre-stretched outside diameter can be 5.0 mm, whereas the stretched diameter can be reduced to an outside diameter of 3.0 mm. Thereafter, the stent can recover to its original or a larger diameter by heating the same to above the glass transition temperature to 40° C.

EXAMPLE 3

| Glass Transition Formulation Polymerized by a Thermal Initiator | |
| --- | --- |
| Isobornyl methacrylate | 5.0 grams |
| Octadecyl methacrylate | 2.0 grams |
| Hexyl methacrylate | 2.7 grams |
| Butanediol dimethacrylate | 0.25 gram |
| USP 245(R) | 0.003 gram |

The above-identified monomers were intermixed with the fifth ingredient, a thermal initiator, polymerized by raising the mixture to a suitable temperature as for example 85° C. Tubular stents were then formed in the manner as hereinbefore described. The stent was then stretched at 32° C., which is slightly above the glass transition temperature of the formulation. While in the stretched condition, the temperature was lowered to 20° C. The stent will recover to its original dimensions by immersing the same in water at a temperature of 37° C. Because of this relatively low glass transition temperature, it is necessary that the stent be kept in a cool state prior to insertion of the same into a vessel. In the embodiments hereinbefore described, they were stable at room temperature.

EXAMPLE 4

| Glass Transition Formulation Polymerized by a UV Initiator | |
| --- | --- |
| Methyl methacrylate | 0.45 gram |
| Polyethyleneglycol methacrylate | 0.34 gram |
| Butyl acrylate | 0.20 gram |
| Ethylene glycol dimethacrylate | 0.01 gram |
| Durocure 1173(R) | 0.002 gram |

The above ingredients were polymerized and formed into cylindrical tube which was cut into stents. The ends of the stent were ground as hereinbefore described and then the stent was stretched at 25° C. which is approximately 38° C. above its glass transition temperature. The stent was then cooled to a −25° C. while in the stretched state. The stent remains in the stretched state as long as its temperature is maintained below the glass transition temperature of −10° C. To recover the stent to its original dimensions, or for example the larger diameter, the stent is allowed to warm up to ambient temperature. Because of the low glass transition temperature for this stent, the stent must be refrigerated until it is ready for use.

EXAMPLE 5

| Glass Transition Formulation Polymerized by a UV Initiator | |
| --- | --- |
| Methyl methacrylate | 0.45 gram |
| Polyethyleneglycol methacrylate | 0.35 gram |
| Isobutyl methacrylate | 0.20 gram |
| Hexanediol dimethacrylate | 0.01 gram |
| Durocure 1173(R) | 0.002 gram |

The mixture of the above-identified monomers were polymerized by ultraviolet radiation. The prepared stent was stretched at 30° C., approximately 5° above the glass transition temperature. While retained in the stretched condition, the temperature of the stent was lowered to 15° C. Such a stent recovers its original dimensions when the temperature rises to 27° C.

EXAMPLE 6

| Glass Transition Formulation Polymerized by a Thermal Initiator | |
|---|---|
| Methyl methacrylate | 0.58 gram |
| Polyethyleneglycol | 0.34 gram |
| Butyl methacrylate | 0.54 gram |
| Hexanedioldimethacrylate | 0.02 gram |
| Benzoin methyl ether | 0.002 gram |

The above-identified mixture was polymerized by ultraviolet radiation to form a cylindrical tube. The tube was cut into stents which were fabricated in the manner hereinbefore described. The stent was stretched at 28° C., slightly above the glass transition temperature to reduce the diameter by a factor of 2. While the stent was held in a stretched condition, the temperature was reduced to 20° C. Because of the low glass transition temperature, the stent was stored at 20° C. until it was ready for use at which time it would recover to its initial diameter with an increase in temperature to the glass transition temperature of approximately 28° C.

EXAMPLE 7

| Main Chain Crystallizable Formulation | |
|---|---|
| Polyoctenylene (Vestenamer(R) Huls Corp.) | 70 grams |
| Polyethylene glycol | 25 grams |
| Triallyl isocyanurate | 5 grams |

The above-identified polymers and the crosslinking agent (triallyl isocyanurate) were blended prior and then introduced into an extruder. The extruder served to intimately blend the polymers and the crosslinking agent and to form a cylindrical tube therefrom. If desired, a rectangular strip can be extruded instead of a cylindrical tube.

To achieve crosslinking in the tube or strip, the tube or strip are irradiated with a 2.5 Mrad electron beam irradiation. The irradiated tube is then stretched at 50° C., which is above the melting point of the polymer formulation. The tube is held in this stretched state while the temperature is lowered to 25° C. This formulation provides a melting point of the main chain. The stent recovers to its prestretched dimensions or a greater diameter by immersing the stent in a normal saline solution at 52° C., the melting point of the main chain.

In a similar manner, the rectangular strip was extruded in the same manner and was heated to a temperature of 50° C. and then wound around a mandril to form a helix or coil approximately 4 mm in outside diameter. While in the coiled configuration, the temperature of the strip was lowered to ambient. The coiled stent was irradiated with 5 Mrads of gamma radiation. After radiation, the stent was stretched to reduce its diameter to 2 mm. While in the stretched state, its temperature was lowered to 25° C. The stretched end recoils to its prestretched dimensions by immersing the coil in a normal saline solution at 50° C.

EXAMPLE 8

| Side Chain Crystallizable Formulation | |
|---|---|
| Methyl methacrylate | 2.0 grams |
| Octadecyl methacrylate | 6.0 grams |
| Isobutyl methacrylate | 2.3 grams |
| Triethylene glycol dimethacrylate | 0.1 gram |
| Perkadox 16(R) | 0.04 gram |

The above-identified monomers were mixed and polymerized at 75° C. in the form of a cylindrical tube. Stents were formed therefrom and stretched from an initial diameter of 2.0 mm to 0.75 mm at 40° C., which is above the melting point of the Octadecyl side chains. While in the stretched state, the stent is cooled to 23° C. Such a stent will recover to its initial dimensions by exposing it to a temperature of 38° C.

EXAMPLE 9

| Glass Transition Formulation Recovered by Adsorption of a Liquid | |
|---|---|
| Methyl methacrylate | 3.0 grams |
| Hydroxyethyl methacrylate | 4.0 grams |
| Butyl methacrylate | 2.8 grams |
| Polyethylene glycol dimethacrylate | 0.04 gram |
| Durocure 1173(R) | 0.0025 gram |

The above-identified monomers with the UV initiator are mixed and then polymerized by ultraviolet radiation, then formed into a cylindrical stent. The stent was stretched at 34° C. above the glass transition temperature of 25–27° C. and then cooled in the stretched state to ambient. The stent recovered to its original dimensions by placing it in water at 28° C. The stent adsorbed approximately 10 percent water by weight. By the adsorption of water, the glass transition temperature of the formulation is lowered to initiate recovery of the stent to its original dimensions.

EXAMPLE 10

| Glass Transition Formulation Recovered by Adsorption of a Liquid | |
|---|---|
| Isobornyl methacrylate | 0.3 gram |
| N-vinyl pyrrolidone | 0.2 gram |
| Butyl acrylate | 0.45 gram |
| Polyethylene glycol dimethacrylate | 0.05 gram |
| Benzoyl peroxide | 0.004 gram |

The above-identified monomers were mixed and polymerized with an ultraviolet source to form a tubular stent. The stent was stretched at 32° C. and cooled to ambient in the stretched state. The stent later recovers to its prestretched dimensions by placing the stretched stent in a normal saline solution at 30° C. The stent adsorbs approximately 15 percent water by weight. In so doing, the glass transition temperature of the stent was lowered below the temperature of the saline solution initiating recovery of the stent to its original dimensions.

EXAMPLE 11

| Recovery by a Change in the pH of the Stent | |
|---|---|
| Methyl methacrylate | 0.35 gram |
| Methacrylic acid | 0.15 gram |
| Hexadecyl methacrylate | 0.45 gram |
| Polyethylene glycol dimethacrylate | 0.05 gram |
| USP 245(R) | 0.004 gram |

The above-identified monomers were intermixed and polymerized by the use of heat at 80° C. to form a tubular stent. The stent was stretched to reduce its diameter from 3 mm to 2 mm at 35° C. The temperature was then reduced to ambient while the stent was in the stretched state. Such a stent recovers its original dimensions by placing the same in a carbonate buffer solution whose pH was 8.4. This was accomplished because the polymer contained acid groups and was subjected to a basic bath to achieve their recovery.

EXAMPLE 12

| Recovery by a Change in the pH of the Stent | |
|---|---|
| Isobornyl methacrylate | 0.2 gram |
| Acrylic acid | 0.2 gram |
| Octadecyl methacrylate | 0.35 gram |
| Polyethylene glycol dimethacrylate | 0.1 gram |
| Perkadox 16(R) | 0.03 gram |
| N-vinyl pyrrolidone | 0.15 gram |

The above-identified ingredients were mixed together to provide a formulation which was polymerized at a temperature of 70° C. The stent was then stretched at 50° C. to reduce its diameter from 5.0 mm to 2.5 mm. While in the stretched state the temperature of the stent was lowered to ambient. Such a stent recovers to its original condition when placed in an aqueous buffer solution having a pH of 8.5.

EXAMPLE 13

| Liquid Crystal | |
|---|---|
| Para cyalohexyl methacrylate | 0.8 gram |
| Octadecyl methacrylate | 0.1 gram |
| Hexanedioldimethacrylate | 0.1 gram |
| Durocure 1173(R) | 0.03 gram |

The above monomers with the UV initiator are mixed and polymerized by UV radiation, then formed into a cylindrical stent. The stent was stretched at 63° C., the liquid crystal transition temperature. While in the stretched state the temperature was lowered to ambient.

Subsequent recovery of the stent to its original dimensions were accomplished by raising the temperature of the stretched stent above 63° C.

From the above examples it can be seen that to impart a memory to the stent, the stent is stretched at a temperature at or above one of the transition identified above. Then while being held in the stretched state, the temperature of the stent is lowered to a temperature below the stretching temperature. Later when the stent is maintained at temperatures below the transition temperature, the stent will remain in a stretched state.

The stent of the present invention can be delivered to a site in a vessel in a body of a patient while it is in the stretched state. This can be accomplished in any suitable manner. For example, as shown in FIG. 4, vessel 31 as shown, for example, can be an arterial vessel in the heart which is provided with a flow passage therein. Let it be assumed that a stenosis 33 has developed in the vessel, and that this stenosis has been reduced by a conventional angioplasty procedure by using an inflated balloon to compress the plaque forming the stenosis to provide enlarged flow passage 34 through the stenosis. Let is also be assumed that it is desirable to place a stent of the present invention in the flow passage 34 of the stenosis 33 to prevent the stenosis 33 to again grow and appear to close off the passage 34. Let it be assumed that a guiding catheter 36 of a conventional type has been introduced into the patient through the femoral artery and advanced into a position adjacent to the stenosis 33. A balloon catheter 37 of a conventional type is utilized. As is well known to those skilled in the art, the balloon catheter is provided with a flexible elongated element 38 which has a balloon inflation lumen (not shown) disposed therein which is in communication with a balloon 39 mounted on the distal extremity of the flexible elongated element 38. The balloon catheter 37 is also provided with a guide wire 41 which can be of a fixed type or a movable guide wire of types well known to those skilled in the art. With the balloon catheter outside of the patient's body, the balloon 39 is deflated and a stent 11 of the type hereinbefore described is slid over the deflated balloon 39 so that it is frictionally engaged by the balloon. The balloon catheter with the stent 11 thereon is then introduced into the guiding catheter which has already been positioned in the patient's body for the angioplasty procedure. The balloon catheter is advanced in the conventional manner so that it is advanced into the stenosis 33. Radiopaque elements (not shown) typically are carried by the balloon catheter in the vicinity of the balloon to facilitate locating the lumen of the balloon catheter as it is advanced in the vessel 31 of the patient. The guide wire 41 is advanced into the flow passage 34, followed by the balloon catheter by advancing the balloon with the stent 11 into the passage 34 so that it is lodged within the stenosis 33 as shown in FIG. 5.

Let it be assumed that the stent 11 is one of the type made in accordance Example 1, and that after it has been positioned as shown in FIG. 4 within the stenosis 33 it is desired to subject the stent 11 to heat in order to cause the stent to assume its recovery diameter, or in other words, the greater diameter in its memory. It can be supplied to the stent by introducing a gas or liquid, preferably a liquid because of its greater heat transfer capabilities, to the balloon inflation lumen in the flexible element 38 and introducing the same into the balloon 39 to inflate the balloon. The heated liquid in the balloon will cause heat to be rapidly transferred to the stent 11 to raise the temperature of the stent until the temperature reaches the glass transition temperature allowing the stent to return to its recovery diameter. This recovery is facilitated by the expansion of the balloon 33 which applies outwardly extending forces to the internal diameter of the stent 11. It should be appreciated that in the event it is desired to stop the flow of a liquid such as blood through the passage 34, that the balloon 39 can be deflated after it has been inflated for a sufficient length of time as for example 2–3 seconds, and thereafter again reinflated until the stent 11 has expanded to firmly engage the stenosis 33 so that it will be frictionally retained therein. The balloon 39 is then deflated, after which the balloon catheter 37 can be removed followed by removal of the guiding catheter 36, so that thereafter all than remains is the stent 11 firmly positioned within the stenosis 33 as shown in FIG. 6 with the flow passage in the stent 11 being opened to the flow passage 32 and permitting a liquid such as blood flowing in the vessel to pass through the stenosis by passing through the passageway 14.

Stents made in accordance with the other examples hereinbefore described can be positioned in a stenosis in the same manner by the use of a balloon catheter, and then permitting the stent to assume its recovery diameter by increasing the temperature of the stent, after it has been positioned in the stenosis, above the stretched temperature as hereinbefore described. As hereinbefore explained, the recovery diameter can be achieved by permitting the stent to adsorb water from a body fluid as for example from the blood in an artery. The stent can also assume its recovery diameter by being subjected to the pH level of the liquid in which the stent is disposed. It is also explained, that the return to the recovery diameter can be aided by outward pressures of the balloon being applied internally of the stent.

For stents which are stretched at or below the body temperature, it is necessary to keep the temperature of the stent below the body temperature prior to insertion of the stent into the vessel of the patient to prevent premature recovery. Once the stent has been positioned in the stenosis in the vessel, the stent is exposed to body temperature by coming into contact with body fluids which will cause the stent to spontaneously recover to its pre-stretched dimensions.

For stents which have been stretched at temperatures above the body temperature, heat from an external source is applied to the stent to raise its temperature to the stretched temperature permitting it to recover its pre-stretched dimensions. As hereinbefore explained, such external heat can be applied by using a heated liquid for inflating and deflating the balloon on the balloon catheter. Alternatively, infrared, microwave or radiofrequency sources as well as resistive heating can be utilized for supplying such external heat to the stent.

For stents which have been stretched at temperatures a below the body temperature, the stent should be maintained at a temperature below the body temperature, as for example it can be refrigerated. When it is desired to utilize the stent, the stent can be placed on the balloon catheter and placed within the guiding catheter. The insulating properties of the guiding catheter can be utilized to protect the stent from the body temperature. Alternatively, the guiding catheter can be provided with a fluid which is below the stretched temperature of the stent. Also, the temperature of the stent can be reduced to a low value by refrigeration so that prior to insertion into the vessel its temperature is substantially less than the temperature of the vessel, making it possible to deploy the stent into the stenosis prior to the time that the temperature has reached the stretched temperature. Thereafter, the stents continued contact with liquids at the body temperature will initiate recovery of the stent to its original dimensions.

In order to enhance ingrowth of intimal and endothelial vessel tissue into the stent, the stent can be made of a porous material to enhance compatibility of the stent with the vessel. Examples of such stents are set forth below.

EXAMPLE 14

| Microporous Stent | |
|---|---|
| Methyl methacrylate | 0.38 gram |
| Polyethylene glycol methacrylate | 0.28 gram |
| Isobutyl methacrylate | 0.20 gram |
| Hexanedioldimethacrylate | 0.03 gram |
| Benzoin methyl ether | 0.003 gram |
| Polyethylene glycol | 0.11 gram |

The above-identified ingredients were thoroughly mixed and then polymerized by the use of ultraviolet radiation to provide a cylindrical stent in the manner hereinbefore described. The stent is immersed in water at 60° C. The water is stirred around the stent. The heated water causes the polyethylene glycol dispersed within the matrix of the stent to be dissolved out of the stent leaving voids and/or pores within the wall of the stent. Typically, the polyethylene glycol will be dissolved out in approximately 120 minutes at that temperature. The stent is then dried and then elevated to a temperature of approximately 55° C. The stent is then stretched to achieve the desired predetermined diameter in the stent. After the predetermined diameter has been reached and while the stent is maintained in a stretched state, the temperature is lowered to ambient. The recovery dimensions of the stent can be initiated by elevating the temperature of the stent to 60° C. or greater.

Such a stent, because of its porosity, promotes ingrowth of intimal and endothelial vessel tissue into the pores of the stent.

EXAMPLE 15

| Microporous Stent | |
|---|---|
| Isobornyl methacrylate | 0.3 gram |
| Hexyl methacrylate | 0.2 gram |
| Hydroxyethyl methacrylate | 0.25 gram |
| Ethylene glycol dimethacrylate | 0.02 gram |
| Polyvinyl pyrrolidone | 0.25 gram |
| AIBN | 0.004 gram |

The above-identified ingredients were polymerized at 75° C. to again form a cylindrical stent in the manner hereinbefore described. The stent is then immersed in water at the ambient temperature in an ultrasonic bath. The polyvinyl pyrrolidone which was dispersed within the polymer matrix is dissolved out of the stent leaving microscopic pores or voids within the wall of the stent. After drying, the stent is stretched after being elevated to a temperature of approximately 42° C. While being held in the stretched state, the temperature was lowered to ambient. Such a stent recovers its original dimensions when subjected to a temperature of 45° C.

The porosity of the wall of the stent again permits the ingrowth of endothelial tissue to enhance compatibility of the stent with the vessel.

Thus it can be seen that stents of the present invention can be formed so as to enhance the ingrowth of endothelial tissue which helps to ensure that the stent will remain in the desired location within the vessel and will not move about in the vessel. Such endothelial vessel tissue growth should occur within approximately four weeks after insertion into the vessel.

In addition, stents of the present invention can be formulated so as to be able to carry a medical agent such as thrombolytic agents, growth factors and slow-release medications. Also, controlled release drug administration can be provided by utilizing the stent as an inert polymeric drug carrier. For example, the drug may be incorporated in a controlled release system as a dispersion in a matrix. The matrix can be formed with a dispersion of uniform drug particles in the biocompatible polymeric materials of the type hereinbefore described in connection with the stent of the present invention. Such stents also can be caused to incorporate the medical agents by causing the stent to imbibe the medical agent such as by exposing the same to a fluid or a liquid carrying the medical agent.

From the foregoing it can be seen that there has been provided a stent incorporating the present invention and an apparatus and method for use therewith which has numerous advantages. It has low protein adsorption and is thus biocompatible. It can be provided with a desired hydrophilicity to improve its compatibility with the vessel. The stent can be made with a desired stiffness so as to match the compliance of the vessel. Because of its built-in memory, the stent need not be physically constrained prior to use to prevent premature recovery. The stents can be made porous to facilitate the ingrowth of intimal and endothelial cells. The stents can be formulated and/or treated so as to carry medical agents which remain with the stent.

More specifically, various formulations can be utilized for preparing polymeric materials which can be used for carrying medical agents in stents of the present invention. The types of formulations which can be used are set forth in the examples below.

EXAMPLE 16

| In-Vitro Release of Ticlopidine From A Polymer Stent | |
|---|---|
| Stent Composition | % |
| Methyl methacrylate | 44.7 |
| Butyl methacrylate | 13.4 |
| Polyethyleneglycol methacrylate (550) | 31.3 |
| Butane dioldimethacrylate | 5.4 |
| Ticlopidine | 4.5 |

Ticlopidine is an anti-platelet agent which helps prevent platelet aggregation and thrombosis associated with restenosis. The monomers listed above are mixed while degasing the mix with dried nitrogen until all Ticlopidine is dispersed. The drug-loaded monomer mix is filled between 2 glass plates to form a 0.2 mm thick film which is then polymerized under ultraviolet light for 16 hours, entrapping the Ticlopidine within the matrix of the film. The film is post cured in a vacuum oven at 40 degrees C. for 4 hours and then extracted in 6% Ticlopidine/alcohol solution for 4 hours to remove unpolymerized monomers. The resultant Ticlopidine proportion approximates 4.5% of the dry weight of the plastic. After drying the extracted film in a vacuum oven at 40 degrees C. for 4 hours a piece of the same is cut and the release of Ticlopidine therefrom is measured in deionized water at 37 degrees C. at 270 nm using a UV spectrophotometer. FIG. 7 shows the cumulative release of Ticlopidine from the plastic matrix as a function of time. It demonstrates that approximately 80% of the dispersed Ticlopidine is released from the stent matrix within two days. At eight days approximately 90% of the total drug is released.

EXAMPLE 17

| In-Vitro Release of Encapsulated Ticlopidine From A Polymer Stent | |
|---|---|
| Stent Composition | % |
| Methyl methacrylate | 44.7 |
| Butyl methacrylate | 13.4 |
| Polyethyleneglycol methacrylate (550) | 31.3 |
| Butane dioldimethacrylate | 5.4 |
| Microcapsules | 4.5 |

In this example Ticlopidine is microencapsulated prior to being homogeneously mixed with the monomers. Encapsulation is achieved by dissolving 1.0 gram of 50/50 polylactide-glycolide in 5.0 grams of dichloromethane. 1.0 gram of Ticlopidine is homogeneously dispersed into this polymer solution. The Ticlopidine solution is added to 20 ml of 5% polyvinyl alcohol and 5% Ticlopidine solution with stirring at 1000 rpm. This is heated to 40 degrees C. for 3 hours while stirring. The microcapsules are collected by pressure filtration, dried at 40 degrees C. in a vacuum oven and then added to the monomer mix with which the plastic matrix is formed as hereinbefore described. Measurement of the released drug is as hereinbefore described. FIG. 8 shows that the release of Ticlopidine is significantly slowed. It takes almost nine days to release approximately 80% of the Ticlopidine instead of the two days it takes to release 80% of the unencapsulated Ticlopidine as in Example 16. It should be appreciated that different encapsulants can be employed to vary release times. Thus, different ratios of polylactic acid to glycolic acid as well as different molecular weights of the polylactic and polyglycolic acid components may be utilized. For example, to effect a longer drug release time higher molecular weights and ratios such as 10/90 or 90/10 may be used.

EXAMPLE 18

| In-Vitro Release of Encapsulated and Unencapsulated Heparin From A Polymer Stent | |
|---|---|
| Stent Composition | % |
| Monomers | 85 |
| Neat Heparin | 5 |
| Heparin Capsules | 10 |

Figure 9:
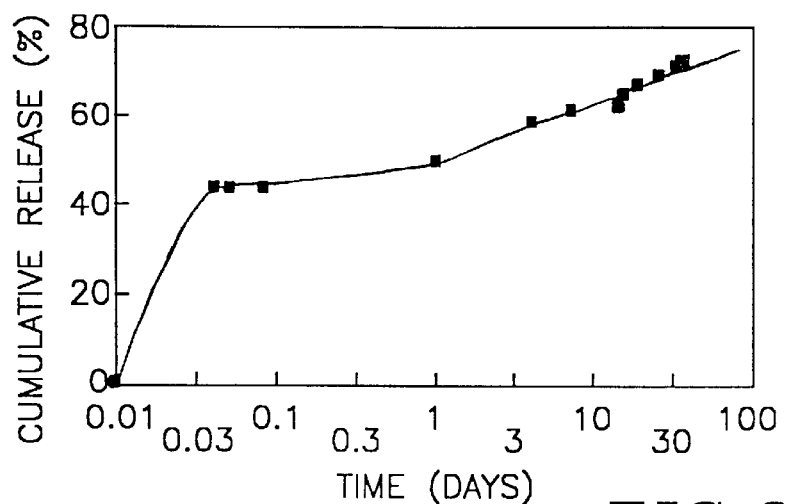
FIG. 9 is a graph demonstrating the in vitro cumulative release of dispersed neat and encapsulated heparin from polymer stent material as a function of time.

Heparin is an anticoagulant which helps prevent thrombosis. A combination of encapsulated heparin and heparin that is simply dispersed into the monomer mix is utilized. The plastic stent is then formed as hereinbefore described. Measurement of the released drug is as hereinbefore described. FIG. 9 demonstrates a triphasic slope when cumulative release is plotted as a function of time. The initial slope represents a release of approximately 40% of the heparin within 2.5 hours, a quick release attributable to the unencapsulated heparin. The next 40–50% of the heparin is released more slowly over a period of approximately one day. This represents initial release of heparin from the capsules. The remaining 10–20% of the heparin is then very slowly released over the subsequent 30 days. This represents heparin being released from capsules from the center of the stent matrix.

EXAMPLE 19

Figure 10:
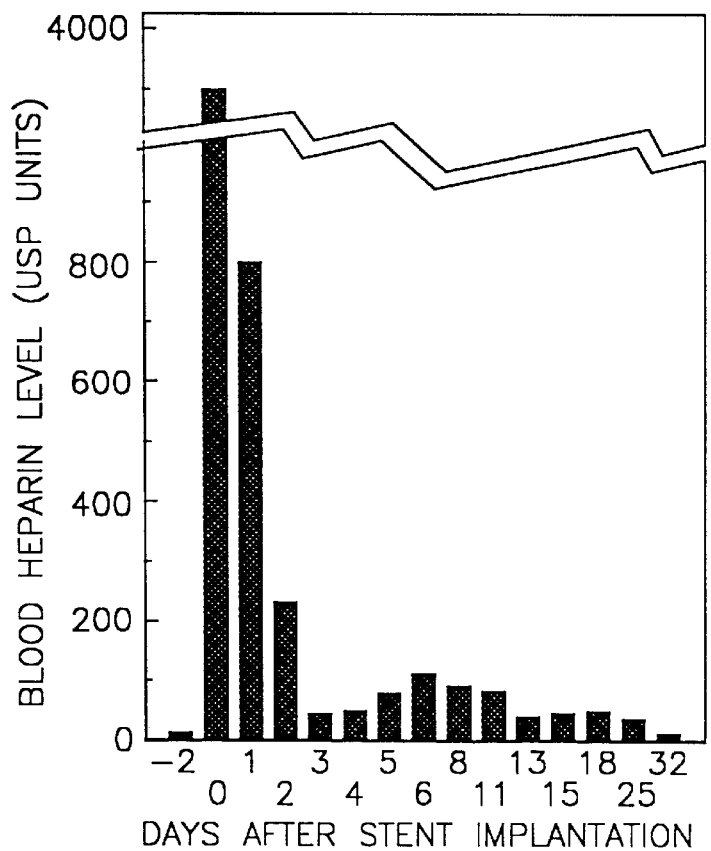
FIG. 10 is graph demonstrating the in vivo release of dispersed heparin from polymer stents implanted in dog coronary arteries as a function of time.

In-Vivo Release of Heparin From Polymer Stents Implanted in Dog Coronary Arteries FIG. 10 demonstrates the release of encapsulated and neat heparin sodium from plastic stents implanted into dog coronary arteries, by displaying blood levels of heparin as a function of time for a period of thirty-two days. Accounting for indigenous heparin, there is 3445 units of heparin released at the end of day one, 795 units at the end of day two, 232 units at the end of day three and 39 units at the end of day four. At the end of day five however, there is 45 units released followed by 78 units at the end of day six and 113 units at the end of day seven. At the end of day nine the release of heparin again decreases to 82 units. These blood levels are attributable to an initial fast release of neat heparin followed by exhaustion of the same, then a measurable amount of encapsulated heparin at day seven followed by another drop.

EXAMPLE 20

| In-Vitro Release of Vitamin E From Stent Materials | |
| --- | --- |
| Stent Composition | % |
| Methyl methacrylate | 44.7 |
| Butyl methacrylate | 13.4 |
| Polyethyleneglycol methacrylate (550) | 31.3 |
| Butane dioldimethacrylate | 5.4 |
| Vitamin E | 4.5 |

Figures 11, 12:
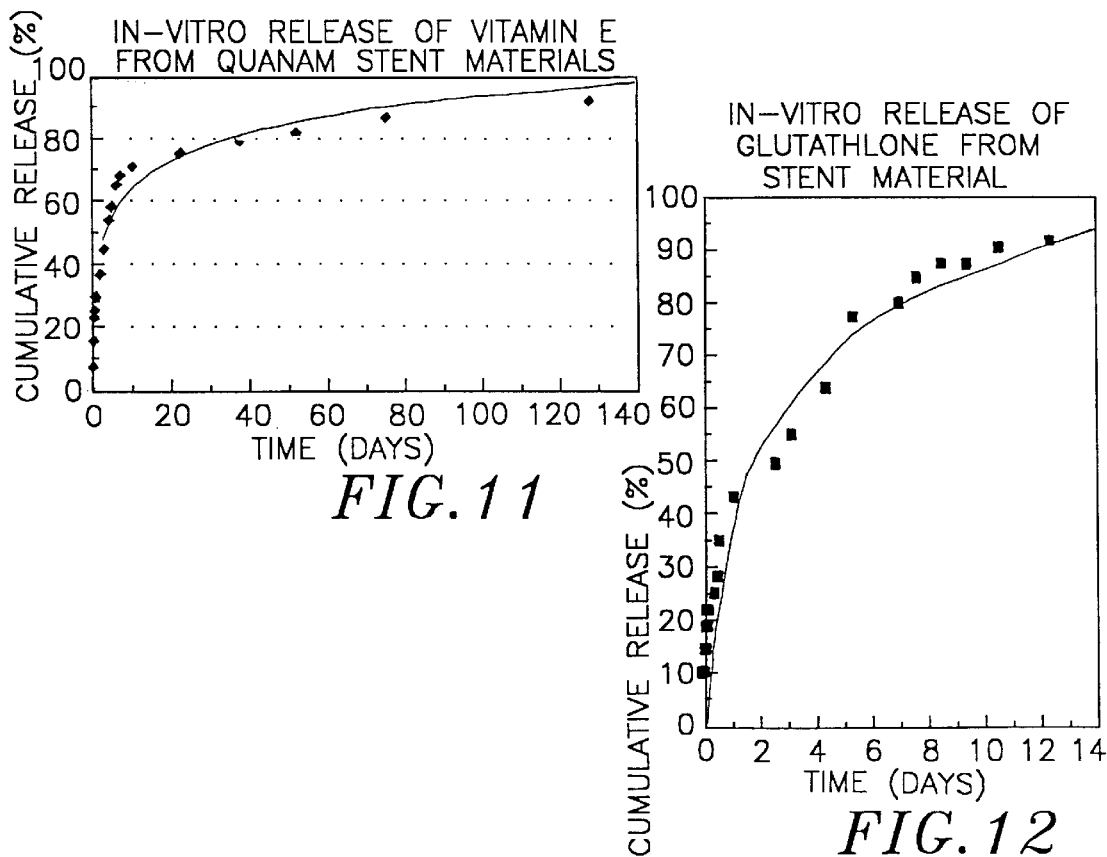
FIG. 11 is a graph demonstrating the in vitro cumulative release of dispersed vitamin E from polymer stent material as a function of time.
FIG. 12 is a graph demonstrating the in vitro cumulative release of dispersed glutathione from polymer stent material as a function of time.

Vitamin E and glutathione are anti-oxidants which are believed to be important in maintaining the health of vascular tissue. Formation of the plastic matrix is as hereinbefore described. Measurement of released Vitamin E is done in a 10% ethanol solution at 37 degrees C. FIG. 11 demonstrates the release of Vitamin E as a function of time. Approximately 60% of the dispersed Vitamin E is released from the stent in ten days with the remaining Vitamin E released over the ensuing 140 days.

EXAMPLE 21

| In-Vitro Release of Glutathione From Stent Materials | |
| --- | --- |
| Stent Composition | % |
| Methyl methacrylate | 44.7 |
| Butyl methacrylate | 13.4 |
| Polyethyleneglycol methacrylate (550) | 31.3 |
| Butane dioldimethacrylate | 5.4 |
| Glutathione | 4.5 |

Formation of the plastic matrix and measurement of the released antioxidant in deionized water is as hereinbefore described. FIG. 12 shows that 35% of the glutathione is released within the first day, 50% by the second day and 90% of total glutathione is released from the stent by fourteen days. This represents another demonstration of an extended controlled drug release from the stent matrix.

EXAMPLE 22

| In Vitro Release of Radioactively Labeled Antisense-Oligonucleotides From Stent Materials | |
| --- | --- |
| Stent Composition | % |
| Methyl methacrylate | 44.7 |
| Butyl methacrylate | 13.4 |
| Polyethyleneglycol methacrylate (550) | 31.3 |
| Butane dioldimethacrylate | 5.4 |
| Macro- and Micro-porous particles | 4.5 |

Antisense-oligonucleotides are genetic blockers which prevent activation of the gene responsible for intimal hyperplasia, a vessel wall abnormality that contributes to restenosis. After entering a cell, antisense-oligonucleotides interfere with messenger RNA (mRNA), thereby arresting protein translation. One such example of an oligonucleotide which operates to block intimal hyperplasia is a 14-MER double stranded phosphothionate DNA fragment oligonucleotide. Double strands are annealed to cause the two strands to be hydrogen bonded. The base pair sequences of each strand are as follows:

```
[primary]  5'
ctagatttcccgcg-3'          (SEQ ID No: 1)

[complement]5'
gatccgcgggaaat-3'          (SEQ ID No: 2)
```

Another such oligonucleotide is as follows:

```
[primary]  5'
gatcaaaagcgcgaatcaaaagcgcgaatc-3'    (SEQ ID No: 3)

[complement]5'
gattcgcgcttttgattcgcgcttttgatc-3'    (SEQ ID No: 4)
```

It should be appreciated that there is no single sequence of a particular antisense oligonucleotide to which use of Applicant's invention is restricted.

Figure 13:
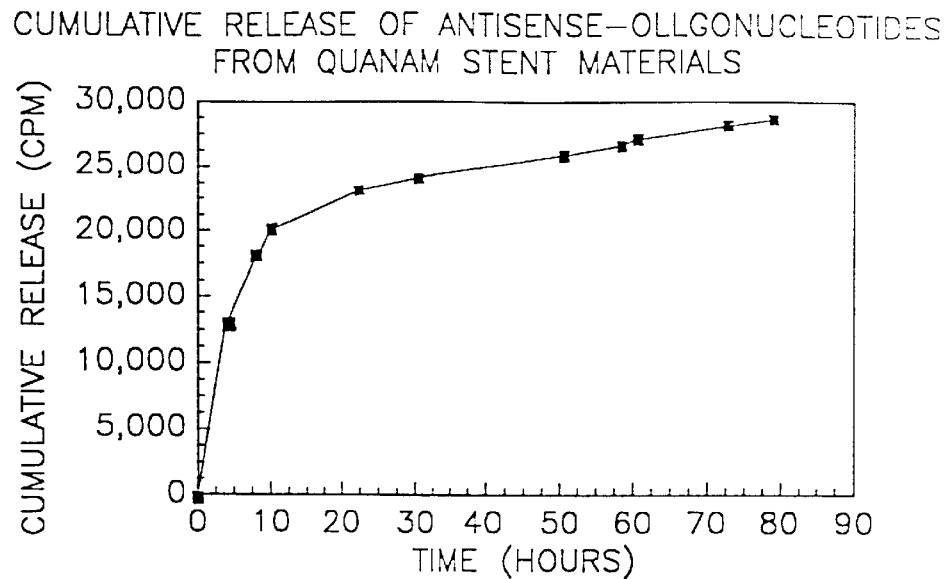
FIG. 13 is a graph demonstrating the cumulative release of dispersed anti-sense oligonucleotide from polymer stent material as a function of time.

In this formulation, the anti-sense oligonucleotide is entrapped in micro- and macro-porous cross-linked polymer particles. Said particles are then dispersed in the stent's polymer matrix. In order to reach the vessel wall the drug must first diffuse from the porous particles and then from the stent matrix. The shape, size and porosity of the carrier particles are determined by their formation. Differences in these characteristics yield different diffusion kinetics for a single drug. In this example 0.35 grams of Oxynex K, a mixture of antioxidants from RONA Chemicals, is diluted with one gram of ethanol and 0.65 grams of micro- and macro-porous cross-linked polystyrene particles. The mean particle size is five microns. This is vigorously stirred until the liquid mixture is absorbed by the particles. The particles are dried in a vacuum oven at 40 degrees C. for four hours to remove the ethanol. 6219 microliters of a radiolabelled Antisense Oligodeoxynucleotides (ODN) solution is added to 0.035 grams of Oxynex-loaded powder and mixed well until the oligonucleotide solution is absorbed by the particles. The particles are dried in an oven at 37 degrees C. for 2 hours after which the antisense ODN/Oxynex loaded-powder is carefully collected. Formation of the plastic stent matrix then proceeds as hereinbefore described. The release of ODN is measured in deionized water solution at 37 degrees C. using a beta scintillation counter. FIG. 13 shows cumulative drug release as a function of time. It demonstrates that approximately 50% of the antisense-oligonucleotide is released after ten hours with the remainder released over the subsequent eighty hours.

EXAMPLE 23

Porous Particular Entrapment of Vitamin E In Stent Materials

In this formulation the overall stent composition and matrix formation is as hereinbefore described with the exception that porous particles are utilized which differ from Example 22. In addition, Vitamin E is entrapped in said porous particles instead of being encapsulated as in Example 20. This is thus another demonstration of the different dispersion techniques available for incorporating a particular drug in the stent matrix.

Specifically, rods made of cross-linked polyacrylates and methacrylates and having a high porosity of approximately 80% are cryogenically ground to yield microscopic, randomly shaped particles with an average particle size of twenty microns. These particles are highly porous and possess very large surface areas of 550 $m^2$/gram. Porosity and surface area of similar particles can range from five to ninety percent and from 20 $m^2$/gram to 700 $m^2$/gram respectively. It should be appreciated that these particles can also be made from almost any polymers which are not dissolved by the plastic monomer mixture, such as polycarbonate, nylons, polyaryletherketones, polybutadene and its copolymers, polysulfones, polyethylenes and their cross-linked copolymers and similar compounds. Such particles can also be inorganic in nature, such as from aluminum oxide, diatomaceous earth, silicas, silicates and the like.

One gram of these highly porous particles is mixed with an ethanol solution of Vitamin E consisting of 0.4 grams of Vitamin E plus one gram of ethanol. The matrices and surfaces of the porous particles absorb the ethanol solution. The particles are then dried in a vacuum oven at 35 degrees C. for four hours to remove the ethanol.

EXAMPLE 24

In Vitro Release of Warfarin From Stent Materials

Figure 14:
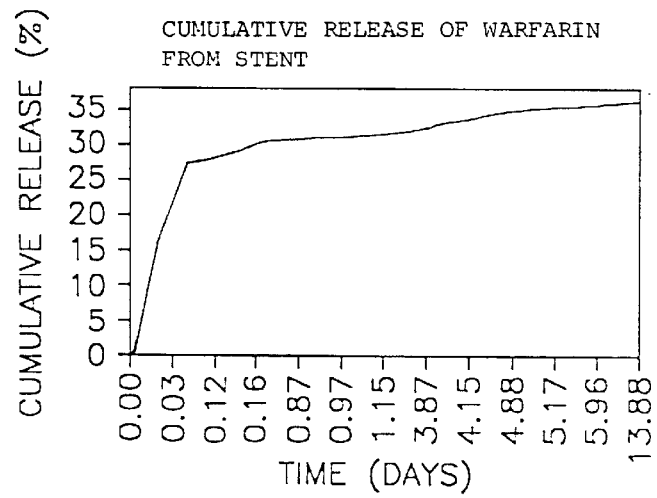
FIG. 14 is a table of data representing the cumulative release of dispersed warfarin from polymer stent material as a function of time.

The next two drugs are anticoagulants which also function as anti-thrombotics. Warfarin is dispersed within the stent matrix and its release measured as hereinbefore described for other drugs. FIG. 14 demonstrates that approximately 15% is released after twenty minutes, 25% is released after seventy-five minutes and approximately 30% of the total Warfarin is released after a period of two hundred and twenty minutes.

EXAMPLE 25

Figure 15:
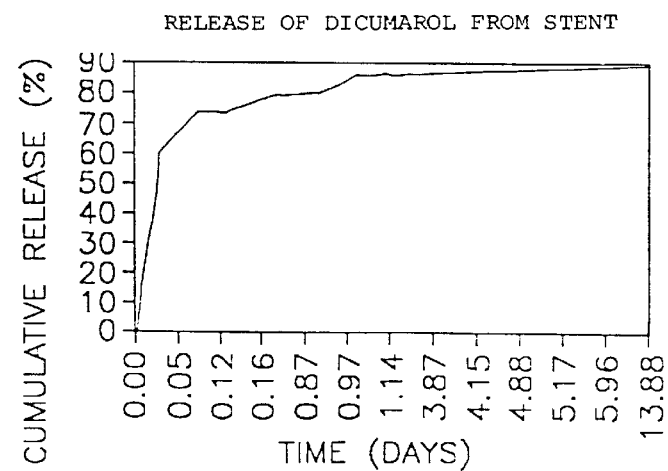
FIG. 15 is a table of data representing the cumulative release of dispersed dicumarol from polymer stent material as a function of time.

Dicumarol is similarly dispersed in the stent matrix and its release measured in a 0.4% sodium hydroxide solution. FIG. 15 shows that 50% of Dicumarol is released after thirty-six minutes. 70% of Dicumarol is released after ninety-one minutes and by 19.5 days, 80% is released from the stent material.

From the foregoing, it can be seen that there has been provided a stent incorporating the present invention and an apparatus and method for use therewith which has numerous advantages. Atherosclerotic vascular disease affecting coronary and peripheral blood vessels is a devastating and burdensome disease, in both personal and societal terms. Restenosis or reblockage of atherosclerotic blood vessels that have been mechanically opened by either surgery or angioplasty is a major impediment to the successful treatment and prognosis of this disease. A significant percent of patients exhibit restenosis within only months after undergoing high-risk, costly procedures to clear their obstructed vessels. Thus, the prevention of restenosis has significant implications.

The restenosis process is attributable to multiple factors. In its early stages there is thrombosis with platelet aggregation at the site of damaged vascular cells. Later, proliferation of cells in the damaged vessel's intimal and medial wall layers exacerbates the process. As such, effective prophylaxis necessitates pharmacological treatment in addition to mechanical stenting. Many of the systemically administered drugs used in such regimens have significant toxic side effects or are eliminated prior to reaching therapeutic levels where they are most effective, at diseased cellular sites. The plastic stent of the present invention can be formulated to incorporate and deliver drugs locally while it performs the mechanical functions of the stent. Unlike common metal stents which can be coated with only small amounts of a drug, plastic matrices offer the ability to disperse and entrap larger amounts of a variety of drugs which effectively interfere with the restenosis process. Furthermore, the numerous polymers into which drugs can be dispersed and the various methods of incorporating multiple drugs into the polymers, along with different forms or quantities of the same drug, provide the opportunity to tailor the site-specific drug regimen to the individual patient's condition and needs. Not only may advantage be taken of different release kinetics for different drugs and different forms of the same drug, but the release kinetics may actually be manipulated. For example, drug diffusion may differ in different polymer matrices. In addition, either free drug particles, microencapsulated drug particles, entrapped drug particles or a combination thereof may be dispersed into the polymer matrix. Microencapsulation and entrapment significantly slow release of a drug. Furthermore, different encapsulants have different dissolution times. Similarly, highly porous particles in which drugs may be entrapped may vary in shape, size and porosity. These cross-linked polymer carriers can be fashioned into spheres or irregularly shaped particles with either micropores or macropores. A given drug will demonstrate different diffusion kinetics from such variants. Drug release may thus be governed not only by drug diffusion through the matrix but also by the dissolution of any microcapsules around the drug and diffusion from various porous, entrapping polymer carriers. Release can actually be programmed to occur when the drugs are most effective, in some cases for prolonged periods of time after stent placement. One drug may be released over the first few days, a second drug over the first few weeks, and third drug may continue to be released for six months or more after stent placement. For example, the stent may be formulated so as to carry heparin to prevent thrombosis. In addition the same may be formulated to simultaneously carry drugs such as Ticlopidine or ReoPro, two anti-platelet agents, or an antisense-oligonucleotide. The latter is an agent that switches off the gene responsible for intimal and medial hyperplasia, an integral part of the restenosis process. It should be appreciated that there are other agents that may be similarly incorporated into the stent such as the anti-oxidants glutathione and Vitamin E, two compounds believed to be important in maintaining the health of vascular tissue and preventing restenosis. Warfarin and Dicumarol, two anticoagulants, may be incorporated into the stent matrix to help prevent thrombosis. In addition, drugs may be utilized that actually break down clots already formed at the site of an injured vessel. Examples of such thrombolytic agents include tissue plasminogen activator, urokinase and streptokinase. Many different types of enzymes may also be incorporated into the matrix to effect reactions that assist in the prevention of restenosis. All such agents may also be dispersed in entrapped, encapsulated or free forms. In addition to varying the proportions of these forms, the types of encapsulation and entrapment may be manipulated so that release is maximized at a time when a drug is most effective yet continues over a time period when the drug remains moderately effective. Optimal dosages and release kinetics for a particular drug depend on the particular case and the patient's risk for restenosis.

The ability to manipulate the properties of the stent and the release of its dispersed drugs enables the creation of a more effective treatment regimen that interferes with multiple steps in the restenosis process. Thus, in addition to functioning as a scaffolding over the lesions in the vessel at risk for restenosis, the stent of the present invention provides timed, very site-specific drug delivery to said lesions, where and when the treatment is most effective.

In general, the polymer compositions can be containing one or more of the following: acrylic acid, methacrylic acid, esters of acrylic acid and methacrylic acid and combinations thereof. Such compositions can also be provided which contain acrylic acid, methacrylic acid, esters of acrylic acid and methacrylic acid with N-vinyl pyrrolidone. Compositions can also be provided containing copolymers of ethylene oxide and vinyl monomers and other compositions which contain acrylamide esters. Other compositions can contain acrylic acid, methacrylic acid, acrylic esters, methacrylic esters, vinyl pyrrolidone and acrylamide esters. These compositions can contain copolymers of vinyl pyrrolidone and monomers such as

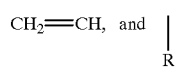

alternatively copolymers of vinyl ether and monomers such as

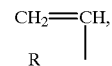

where $R=C_nH_{(2n+1)}$, and alternatively copolymers of maleic anhydride. Compositions also can be provided containing blends of polymers such as polyethylene oxide, Vestenimer® (polyoctenylene), polyethylene, polysiloxanes, nylons and polyesters. Other compositions can contain polymers and plasticizers which depress the glass transition temperature within the temperature range of −50° C. to +100° C.

What is claimed:

1. A stent for use in a lumen defined by a wall of a vessel of a patient having a body with the vessel therein, comprising a hollow substantially cylindrical member formed of a biocompatible composition, said composition being in the form of a polymer matrix, at least one medical agent in a weight up to 90% of the total weight of said member dispersed uniformly throughout said polymer matrix whereby when said stent is disposed in the lumen said at least one medical agent is released at a controlled release rate from the member into said vessel, it must be dissolved in the polymer matrix and thereafter diffuse through the polymer matrix, said controlled release rate extending over a period of time after said lumen stent is inserted into said and being controlled solely by the rate of diffusion of the medical agent from the stent.

2. A stent as in claim 1 wherein said at least one medical agent has been absorbed by said biocompatible composition.

3. A stent as in claim 1 wherein said polymer matrix has a transition characteristic therein whereby when the transition characteristic is activated the substantially cylindrical member will change its dimensions in all directions and assume a greater diameter than the initial predetermined diameter and come into engagement with the wall of the vessel to form a flow passage in the lumen of the vessel.

4. A stent as in claim 1 wherein said member has an initial built-in elastic predetermined diameter which is less than the diameter of the lumen in the vessel so that the substantially cylindrical member can be inserted into the lumen of the vessel, said polymer matrix of said cylindrical member also having a memory based on a transition provided therein of a diameter greater than the built-in elastic predetermined diameter and at least as great as the diameter of the lumen of the vessel, said polymer matrix being characterized in that it will change its dimensions in all directions and will assume the greater diameter in its memory and move into engagement with the wall of the vessel upon the occurrence of one or more of the following conditions selected from the group consisting of: (a) adsorption of heat by the plastic material; (b) adsorption of a liquid by the plastic material; and (c) a change in the pH in the liquid in which the plastic member is disposed.

5. A stent as in claim 1 wherein said member has an initial built-in elastic predetermined diameter which is less than the diameter of the lumen in the vessel so that the substantially cylindrical member can be inserted into the lumen of the vessel, said member also having a memory based on a thermal transition provided therein of a diameter greater than the initial predetermined diameter and at least as great as the diameter of the lumen of the vessel, said member being characterized in that it will assume the greater diameter and move into engagement with the wall of the vessel upon the absorption of heat by the polymer matrix to activate said thermal transition which is achieved by one of the following selected from the group consisting of (a) a melting point of the main chain; (b) a melting point of the side chain; (c) a glass transition temperature; (d) a liquid crystal transition; and (e) a local mode molecular transition.

6. A stent as in claim 5 wherein said polymer matrix has a thermal transition which is achieved by one of the following: (a) a melting point of the main chain; (b) a melting point of a side chain; (c) a glass transition temperature; (d) a liquid crystal transition; and (e) a local mode molecular transition.

7. A stent as in claim 6 wherein said encapsulating means is selected so that the release extends over a time period from several hours to one year.

8. A stent as in claim 1 wherein said medical agent is an anti-platelet drug dispersed in said matrix in a weight of 1% to 50% of said total weight of said matrix so that 80% of said anti-platelet drug diffuses to said wall of a vessel by nine days and 90% by 12 days.

9. A stent as in claim 1 wherein said medical agent is an anticoagulant dispersed in said matrix in a weight of 1% to 50% of said total weight of said matrix so that 80% of said anticoagulant diffuses to said wall of a vessel by two to four weeks.

10. A stent as in claim 1 wherein said medical agent is an anti-oxidant dispersed in said matrix in a weight of 1% to 50% of said total weight of said matrix so that 60% of said anti-oxidant diffuses to said wall of a vessel by ten days and 90% by six months.

11. A stent as in claim 1 wherein said at least one medical agent is Ticlopidine, said Ticlopidine being dispersed in said matrix in a weight of 1% to 50% of said total weight of said matrix so that 80% of said Ticlopidine diffuses out of said matrix to said wall of a vessel by two days and 90% by eight days after insertion of said stent into said vessel.

12. A stent as in claim 1 wherein said at least one medical agent is Ticlopidine, said Ticlopidine being dispersed in said matrix in a weight sufficient so that 80% of said Ticlopidine diffuses out of said matrix to said wall of a vessel by two days and 90% by eight days after insertion of said stent into said vessel.

13. A stent as in claim 1 wherein said at least one medical agent is Heparin, said Heparin being dispersed in said matrix in a weight of 1% to 50% of the total weight of said matrix and wherein 15% to 50% of said Heparin is encapsulated so that 20% to 40% of said Heparin diffuses out of said matrix to said wall of a vessel by two to four hours, an additional 20% to 40% by one day and the remainder of said Heparin by 20 to 30 days after insertion of said stent into said vessel.

14. A stent as in claim 1 wherein said at least one medical agent is Vitamin E, said Vitamin E being dispersed in said matrix in a weight of 1% to 50% of the total weight of said matrix so that 60% of said Vitamin E diffuses out of said matrix to said wall of a vessel by ten days and 80% to 100% by six months after insertion of said stent into said vessel.

15. A stent as in claim 1 wherein said at least one medical agent is glutathione, said glutathione being dispersed in said matrix in a weight of 1% to 50% of the total weight of said matrix so that 20% to 40% of said glutathione diffuses out of said matrix to said wall of a vessel by one day, 50% to 60% by two days, and 90% to 100% by 14 days after insertion of said stent into said vessel.

16. A stent as in claim 1 wherein said at least one medical agent is Warfarin, said Warfarin being dispersed in said matrix in a weight sufficient so that 5% to 25% of said Warfarin diffuses out of said matrix to said wall of a vessel by 45 minutes, 25% to 30% by two to three hours and 30% to 50% by two to three weeks after insertion of said stent into said vessel.

17. A stent as in claim 1 wherein said at least one medical agent is Dicumarol, said Dicumarol being dispersed in said matrix in a weight sufficient so that 40% to 60% of said Dicumarol diffuses out of said matrix to said wall of a vessel by 30 to 90 minutes, 50% to 70% by one-half to two days and 60% to 100% by two to three weeks after insertion of said stent into said vessel.

18. A stent as in claim 1 wherein said encapsulating means further comprises a biodegradable polymer.

19. A stent as in claim 1 wherein said encapsulating means further comprises a copolymer, said copolymer being formed of the components polylactic and polyglycolic acid in a ratio of polylactic acid to polyglycolic acid ranging from 5 to 95.

20. A stent as in claims 1 wherein said at least one medical agent is selected from the group consisting of
 (a) Ticlopidine;
 (b) Heparin;
 (c) Glutathione;
 (d) Anti-sense nucleotide;
 (e) Vitamin E
 (f) Warfarin
 (g) Dicumarol
 (h) ReoPro
 (i) tissue plasminogen activator
 (j) Urokinase
 (k) Streptokinase
 (l) enzymes.

21. A stent as in claim 1 wherein said entrapment means is selected so that said diffusion extends over a time period from several hours to one year.

22. A stent as in claim 1 wherein said entrapment means further comprises using micro- and macro-porous randomly shaped particles, said particles having an average particle size ranging from 5 microns to 50 microns in diameter and having an average surface area ranging from 20 $m^2$/gram to 700 $m^2$/gram, said particles being made from compounds selected from the group consisting of (a) polyacrylates; (b) polystyrenes; (c) methacrylates; (d) polycarbonate; (e) nylons; (f) polyaryletherketones; (g) polybutadene; (h) polybutadene copolymers; (i) polysulfones; (j) polyethylenes; (k) aluminum oxide; (l) diatomaceous earth; (m) silicas; and (n) silicates.

23. A stent as in claim 1 wherein said medical agent is an anti-sense nucleotide dispersed in said matrix in a weight of 1% to 50% of said total weight of said matrix so that 30% to 60% diffuses out of said matrix to said wall of a vessel by one day and the remainder within one week.

24. A stent as in claim 13 wherein said Ticlopidine is dispersed in said matrix in a weight of 1% to 50% of said total weight of said matrix, 90% to 100% of said Ticlopidine is encapsulated and said copolymer is formed of said components in a ratio of half-and-half so that 80% of said Ticlopidine diffuses out of said matrix to said vessel by nine days and 90% by 12 days after insertion of said stent into said vessel.

25. A stent as in claim 22 wherein said at least one medical agent is an anti-oxidant, said anti-oxidant being dispersed in said matrix in a weight of 1% to 50% of said total weight of said matrix and 80% to 100% of said anti-oxidant being entrapped so that 40% of said anti-oxidant diffuses out of said matrix to said wall of a vessel by 12 hours and the remainder by four months after insertion of said stent into said vessel.

26. A stent as in claim 22 wherein said at least one medical agent is an anti-sense oligonucleotide, said anti-sense oligonucleotide being dispersed in said matrix in a weight of 1% to 50% of the total weight of said matrix and 80% to 100% of said anti-sense oligonucleotide being entrapped so that 30% to 60% of said anti-sense oligonucleotide diffuses out of said matrix to said wall of a vessel by seven to ten hours and the remainder of said anti-sense oligonucleotide by three to four days after insertion of said stent into said vessel.

27. A stent for use in a lumen defined by a wall of a vessel of a patient having a body with the vessel therein, comprising a hollow substantially cylindrical member formed of a biocompatible composition in the form of a polymer matrix and having an outer surface, said polymer matrix carrying at least one medical agent uniformly dispersed in said polymer matrix and which is at least partially disposed below the surface of said member so that said at least one medical agent is released from the member by being dissolved and then diffusing through the polymer matrix at controlled release rate extending over a period of time after said stent is inserted into the lumen, said member being free of biodegradable material whereby said controlled release is determined solely by the rate diffusion of the medical agent from the stent.

28. A stent as in claim 27 wherein said medical agent is incorporated as a component of a multi-component biocompatible composition for the stent.

* * * * *

SEQUENCE LISTING

```
<160> NUMBER OF SEQ ID NOS: 4

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:
      anti-sense,double stranded,  linear
      oligonucleotide

<400> SEQUENCE: 1
ctagatttcc cgcg                                                    14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence:
      anti-sense,double stranded,  linear
      oligonucleotide

<400> SEQUENCE: 2
gatccgcggg aaat                                                    14

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      anti-sense,double stranded,  linear
      oligonucleotide
```

```
-continued

<400> SEQUENCE: 3
gatcaaaagc gcgaatcaaa agcgcgaatc                              30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      anti-sense,double stranded,  linear
      oligonucleotide

<400> SEQUENCE: 4
gattcgcgct tttgattcgc gcttttgatc                              30
```